United States Patent
Chen et al.

(10) Patent No.: US 10,413,727 B2
(45) Date of Patent: *Sep. 17, 2019

(54) HEARING AUXILIARY DEVICE AND HEARING AUXILIARY PROCESSING METHOD

(71) Applicants: Kuang-Chao Chen, New Taipei (TW); SILICON MOTION, INC., Hsinchu County (TW)

(72) Inventors: Kuang-Chao Chen, New Taipei (TW); Kuo-Liang Yeh, Hsinchu County (TW)

(73) Assignees: Kuang-Chao Chen, New Taipei (TW); SILICON MOTION, INC., Hsinchu County (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/870,430

(22) Filed: Jan. 12, 2018

(65) Prior Publication Data

US 2018/0133476 A1 May 17, 2018

Related U.S. Application Data

(63) Continuation of application No. 15/154,547, filed on May 13, 2016.

(30) Foreign Application Priority Data

May 14, 2015 (TW) .............................. 104115414 A

(51) Int. Cl.
*A61N 1/36* (2006.01)
*A61N 1/05* (2006.01)
*H04R 25/00* (2006.01)

(52) U.S. Cl.
CPC ....... *A61N 1/36036* (2017.08); *A61N 1/0541* (2013.01); *H04R 25/606* (2013.01); *H04R 25/70* (2013.01); *H04R 2460/13* (2013.01)

(58) Field of Classification Search
CPC ................................................... A61N 1/36032
See application file for complete search history.

(56) References Cited

U.S. PATENT DOCUMENTS

| | | | | |
|---|---|---|---|---|
| 4,352,960 A | * | 10/1982 | Dormer | A61N 1/372 607/57 |
| 5,913,815 A | * | 6/1999 | Ball | H04R 25/606 600/25 |
| 7,983,435 B2 | * | 7/2011 | Moses | H04R 25/606 381/326 |
| 2002/0150268 A1 | * | 10/2002 | Miller | H04R 25/606 381/191 |

(Continued)

*Primary Examiner* — Carl H Layno
*Assistant Examiner* — Jennifer L Ghand
(74) *Attorney, Agent, or Firm* — Chun-Ming Shih

(57) ABSTRACT

Disclosed is a hearing auxiliary device for helping a person with hearing impairment to obtain hearing information. The hearing auxiliary device includes a bone conduct transceiver, a receiver and a driver. The bone conduct transceiver converts a sound raw data to a bone conduct signal. The receiver is installed to an inner ear portion of the person with hearing impairment, and the receiver receives the bone conduct signal and converts the bone conduct signal to a sound restoration signal. The driver sends out a physical signal according to the sound restoration signal, in order to let the person with hearing impairment to obtain a hearing signal.

16 Claims, 7 Drawing Sheets

(56) References Cited

U.S. PATENT DOCUMENTS

| | | | |
|---|---|---|---|
| 2004/0093040 A1* | 5/2004 | Boylston | A61N 1/36036 607/57 |
| 2005/0033384 A1* | 2/2005 | Sacha | A61N 1/36036 607/57 |
| 2006/0018497 A1* | 1/2006 | Kornagel | H04R 25/552 381/315 |
| 2007/0191673 A1* | 8/2007 | Ball | H04R 25/606 600/25 |
| 2008/0008341 A1* | 1/2008 | Edwards | H04R 25/552 381/315 |
| 2008/0205659 A1* | 8/2008 | Fischer | H04R 25/407 381/23.1 |
| 2009/0138062 A1* | 5/2009 | Balslev | A61B 5/123 607/55 |
| 2009/0281367 A1* | 11/2009 | Cho | H04R 25/606 600/25 |

\* cited by examiner

HEARING AUXILIARY DEVICE AND HEARING AUXILIARY PROCESSING METHOD

CROSS-REFERENCE TO RELATED APPLICATIONS

This application is a continuation of U.S. patent application Ser. No. 15/154,547, "HEARING AUXILIARY DEVICE AND HEARING AUXILIARY PROCESSING METHOD" filed May 13, 2016, which claims priority claim under 35 U.S.C. § 119(a) on Taiwan Patent Application No. 104115414 filed on May 14, 2015, the entire contents of which are hereby incorporated by reference.

BACKGROUND

Technical Field

The present invention relates to a hearing auxiliary device and a hearing auxiliary processing method, and particularly relates to a hearing auxiliary device that can be installed to an inner ear through some components and a hearing auxiliary processing method.

Related Art

A lot of people, when born, lose hearing because of genetic defects or because of traumas or diseases. For those children suffer from hearing loss, it is critical to speech and language development. Therefore, how to provide hearing reconstruction for people who cannot hear is a very valuable job.

DISCLOSURE OF THE INVENTION

In view of the demand for hearing reconstruction, the present invention puts forward a hearing auxiliary device and a hearing auxiliary processing method, for assisting in reconstructing hearing.

According to a first embodiment of the present invention, a hearing auxiliary device is provided, for helping a person with hearing impairment to obtain hearing information. Such a hearing auxiliary device includes a bone conduct transceiver, a receiver and a driver. The bone conduct transceiver converts a sound raw data to a corresponding bone conduct signal. The receiver is installed to an inner ear portion of the person with hearing impairment, and the receiver receives the bone conduct signal and converts the bone conduct signal to a sound restoration signal. The driver sends out a physical signal according to the sound restoration signal, in order to let the person with hearing impairment to obtain a hearing signal.

According to one embodiment, the receiver and/or the driver can be installed to an through hole of the eardrum of the person with hearing impairment, and the receiver and/or the driver are/is supported through the through hole of the eardrum.

In one embodiment, the driver is installed to a cochlea of the person with hearing impairment, and the driver has multiple electrodes, for generating electric shocks as a physical signal to stimulate different positions of the cochlea correspondingly to different frequency.

In addition, in order to improve the signal quality, the bone conduct signal can undergo compression and error-correcting code processing. Moreover, due to cranial electrical characteristics of each person, the bone conduct transceiver may further include a parameter adjuster, and through the parameter adjuster, an optimization processing can be made for cranial electrical characteristics of the person with hearing impairment. The adjustment can be finely tuned through a user or assistance of a physician and an assistant.

Compared with the previous practice, bone conduct vibration is directly used to stimulate eardrums, auditory ossicles and other hearing organs, and the practice of the present invention can perform processing for bone conduct signals, to generate suitable restoration signals. For example, for a person completely hearing nothing, as the traditional bone conduction manner may not directly cause generation of hearing, at this point, it is feasible to analyze a bone conduct signal through a receiver and convert the bone conduct signal to a corresponding restoration signal. At this point, the restoration signal can be used to drive the driver installed into the cochlea of the user, for example, electrodes are implanted into the cochlea, to let the user produce hearing in the brain by directly stimulating cochlear auditory nerves through tiny currents.

In another example, the eardrums or auditory ossicles and other hearing organs of the user can still operate, but only hearing is relatively poor. At this point, it is feasible to install the receiver and/or the driver to through hole of the eardrum and provide support by through hole walls. When the receiver receives the bone conduct signal and interprets and restores the bone conduct signal into a restoration signal, the restoration signal generates an air-vibrating sound signal with an appropriate size according to hearing of the user, to stimulate hearing organs of the user and let the user produce hearing.

There are many manners in which the bone conduct receiver receives sound information, for example, the sound is received directly with a microphone. In addition, it is also feasible to receive sound signal sources in various wirelesses or wired manners, for example, a sound raw data is received from mobile phones, external microphones or various media players. Besides, as the user per se may speak, a sound may also be received through the bone conduct receiver. Moreover, the receiver may also be directly designed to be capable of collecting bone conduct signals brought about through bone conduction when the user per se speaks.

Another practice is that the parameter adjuster of the bone conduct transceiver sends a testing signal to the receiver, the bone conduct transceiver receives a testing result from the receiver, and the bone conduct transceiver adjusts the bone conduct signal according to the testing result.

The bone conduct transceiver can be installed to a pair of glasses, to allow the person with hearing impairment to wear it in a manner of glasses. An alternative practice is that a metal sheet can be implanted into the scalp and the bone conduct transceiver can be attached to an outer surface of the scalp of the person with hearing impairment through magnetic force.

Human can recognize the small differences between the sounds received by different ears, and establish perception for a three-dimensional space. The bone conduct transceiver can have a first transceiving component and a second transceiving component. The first transceiving component and the second transceiving component is disposed respectively to two ears of the person with hearing impairment. Moreover, to avoid that the first transceiving component and the second transceiving component interfere with each other in signal transmission, the bone conduct signal from the first transceiving component and the second transceiving component have a transmitting shift that is staggered apart, for example, the signal is transmitted in a manner of time-division multiplexing.

In another practice, the bone conduct transceiver has a first transceiving component and a second transceiving component. The first transceiving component and the second transceiving component is respectively disposed correspondingly to two ears of the person with hearing impairment. The first transceiving component and the second transceiving component may employ different signal aspects, to avoid that the first transceiving component and the second transceiving component interfere with each other in signal transmission. For example, the first transceiving component and the second transceiving component use carriers at different frequencies to carry the bone conduct signal, and through the arrangement of different signal aspects, mutual interference between signals is avoided.

Bone conduction is a sound conduction manner, that is, sound waves are transferred by converting sounds to mechanical vibration at different frequencies and through a person's skull, bony labyrinth, lymph fluid of coclea, spiral organs, auditory nerves and hearing center. Contrast to generate sound waves through a vibrating diaphragm, bone conduction saves many steps of sound wave transmission and could achieved clear sound restoration in noisy environments. Furthermore, the sound waves may not be affected other people because of diffusion in the air.

A bone conduct technology is divided into a bone conduct speaker technology and a bone conduct microphone technology.

The technique of bone conduct speaker is used for receiving sounds, in other way of speaking this technique is meant for ones to hear. The principle of air conduction speaker is to convert electric signals to sound waves (vibrating signals) and transmit to auditory nerves. On the other hand, the principle of the bone conduct speaker is to directly convert electric signals to sound waves (vibrating signals), and the sound waves are transmit to auditory nerves through bones. In these two methods, the transmitting mediums of the sound waves (vibrating signals) are different.

The technique of bone conduct microphone is used for receiving sounds, in other way of speaking this technique is meant for ones to hear. Air conduction transmitting transfers sound waves to a microphone through air, while bone conduction transmitting transfers sound waves directly through bones.

Specifically, the implementation example can be actually made into an external electronic ear device, used in an artificial ear system. The external electronic ear device includes a housing, an external magnet, a microphone, a processing circuit and a wireless circuit.

The external magnet is installed to a predetermined position at the housing, used to interact with a receiver magnet installed to an inner side of scalp of a user. The housing could be attached to the outer surface of the scalp of the user. The receiver magnet belongs to an implanted artificial ear device. The microphone is installed to a predetermined position of the housing, used to receive an outside sound and generate a corresponding sound signal. The microphone may be various directed or undirected reception devices, and can convert an outside sound to a corresponding sound signal. The microphone may be one or may be a combination of multiple microphones. The processing circuit is installed at the housing and converts the sound signal to a bone conduct signal. The processing signal may include a microcontroller, or an Application Specific Integrated Circuit (ASIC). The processing signal may be totally or partly hardware circuit logic to match corresponding software logic. The bone conduct signal is transferred to the implanted artificial ear device, and the implanted artificial ear device converts an electrode driving signal to multiple electrode currents, that is, more than one electrode current. Through the corresponding multiple electrodes, multiple electrical stimulations are produced at a cochlear nerve conduction part, to cause the user to produce a hearing corresponding to the outside sound.

In practice, the housing has a shell shape, and the shell shape can be tailor-made for a the user according to the attaching position of the head and the color and shape of the housing could be substantially similar to those of the head attaching position, so that the shell shape is not easy to perceive.

In addition, wigs may also be attached to the housing, so that the shell shape of the housing is not easy to perceive.

DETAILED DESCRIPTION

Figure 1:
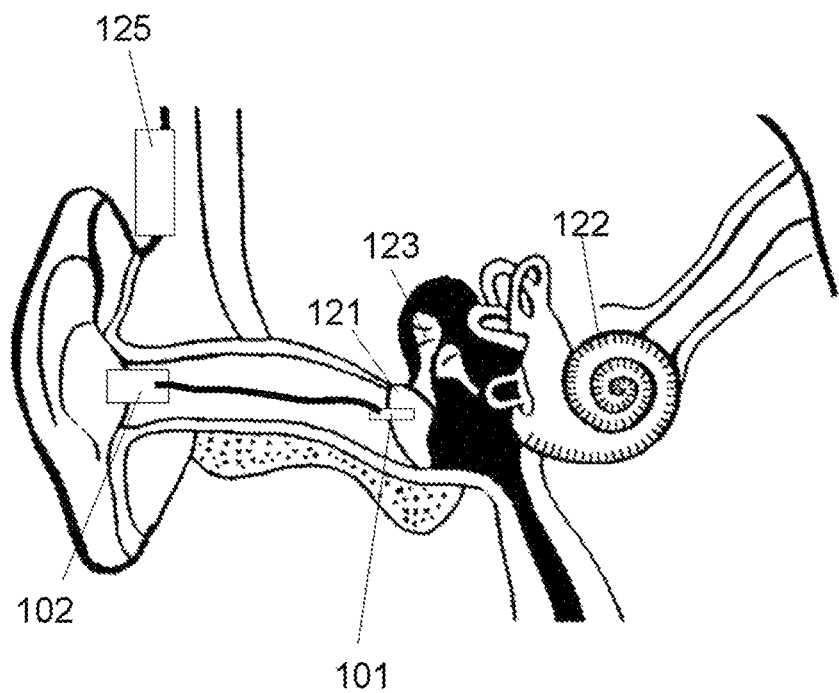
FIG. 1 illustrates a first embodiment of a hearing auxiliary device.

Referring to FIG. 1, FIG. 1 illustrates an embodiment of a hearing auxiliary device. In this embodiment, the hearing auxiliary device includes a bone conduct transceiver 125 and a receiving driving module 101.

Figure 2:
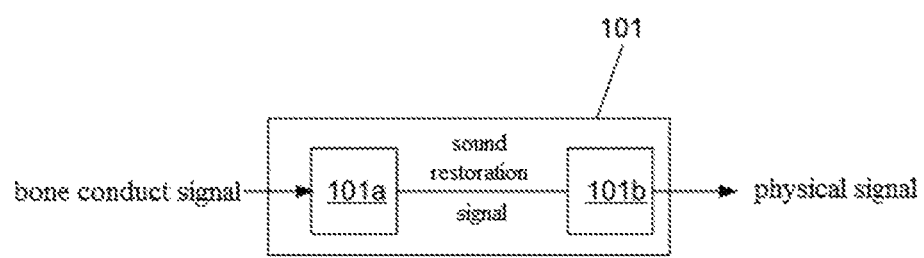
FIG. 2 illustrates a circuit block diagram of a receiving driving module in the first embodiment.

As shown in FIG. 1 and FIG. 2, the bone conduct transceiver 125 receives a sound raw data, and converts it to a bone conduct signal. Then, transfers the bone conduct signal to the receiving driving module 101 by employing a bone conduct principle.

As shown in FIG. 2, the receiving driving module 101 includes a receiver 101*a* and a driver 101*b*. The receiving driving module 101 receives the bone conduct signal by receiver 101*a* and converts the bone conduct signal to a sound restoration signal correspondingly. Then, driving the corresponding driver 101*b* to generate a sound physical signal according to the sound restoration signal, to let hearing organs of the user be stimulated by the physical signal to obtain a hearing signal, thus producing corresponding hearing.

The receiving driving module 101 is further connected with a battery module 102 to obtain power. A charging module is disposed on a side nearby the outside of the ear, in order to charge through another wired or wireless charging device, when the battery module 102 running out of power.

In this example, the receiving driving module 101 is placed on a through hole of an eardrum 121. Specifically, its receiver 101*a* may be made as columnar. The through hole is opened on the eardrum 121 could be made by a surgery, and the receiver 101*a* is installed to the through hole of the eardrum 121. Cell characteristics of the eardrum will rapidly recover for fit. Therefore, during recovering, through hole will fix and provide support for the columnar receiver 101a placed within.

As the receiving driving module 101 is really close to the auditory ossicles and is directly located on the eardrum, therefore the receiving driving module 101 only need to send tiny sound wave vibration as a physical signal, the corresponding hearing organ can be affected to obtain a hearing signal. The hearing organ could be for example, the eardrum 121, the auditory ossicles 123 and the cochlea 122, to produce a chain reaction of hearing.

Figure 3:
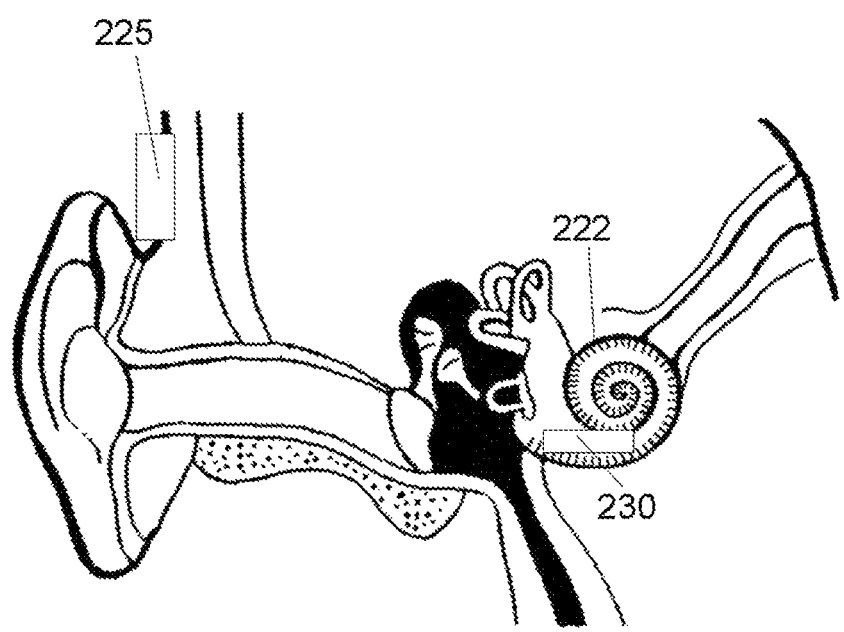
FIG. 3 illustrates a second embodiment of a hearing auxiliary device.

Referring to FIG. 3, it illustrates another embodiment of present invention. In this embodiment, a driver 230 may be installed to a cochlea 222 of the person with hearing impairment. The driver 230 has multiple electrodes for generating electric shocks as a physical signal to stimulate different positions of the cochlea 222 correspondingly to different frequency, thereby obtaining a hearing signal to produce hearing. A bone conduct transceiver 225 converts a sound raw data to a bone conduct signal, and employs by the bone conduction to the driver 230, the driver 230 converts the received bone conduct signal to a corresponding signal, to drive the driver 230 in the cochlea 222 to produce hearing.

Figure 4:
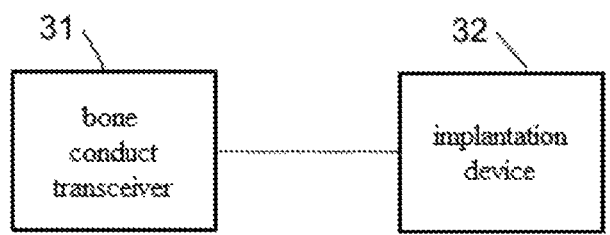
FIG. 4 illustrates an architectural diagram of an embodiment of a hearing auxiliary device.

Referring to FIG. 4, it illustrates an architectural diagram according to an embodiment of the present invention. In FIG. 4, the bone conduct transceiver 31 receives and converts a sound raw data to a bone conduct signal, and the bone conduct signal may be a signal undergoing compression and error-correcting code. Through the bone conduction manner, the bone conduct transceiver 31 transfers the bone conduct signal to an implantation device 32. The implantation device 32 may include, for example, the above said receiver, the driver and other related components. The implantation device 32 is placed in an inner ear position. The implantation device 32 receives the bone conduct signal and amplifies the received bone conduct signal to corresponding sound wave vibration through translation, or outputs a corresponding current signal, to trigger corresponding electrodes placed in the cochlea.

In addition, the bone conduct transceiver 31 may further include a parameter adjuster, and through the parameter adjuster, an optimization processing can be made for cranial electrical characteristics of the person with hearing impairment. Alternatively, the parameter adjuster sends a testing signal to the receiver (e.g., 101a of FIG. 2), and the bone conduct transceiver receives a testing result from the receiver, and the bone conduct transceiver adjusts the bone conduct signal according to the testing result, to optimize the bone conduct signal.

Figure 5:
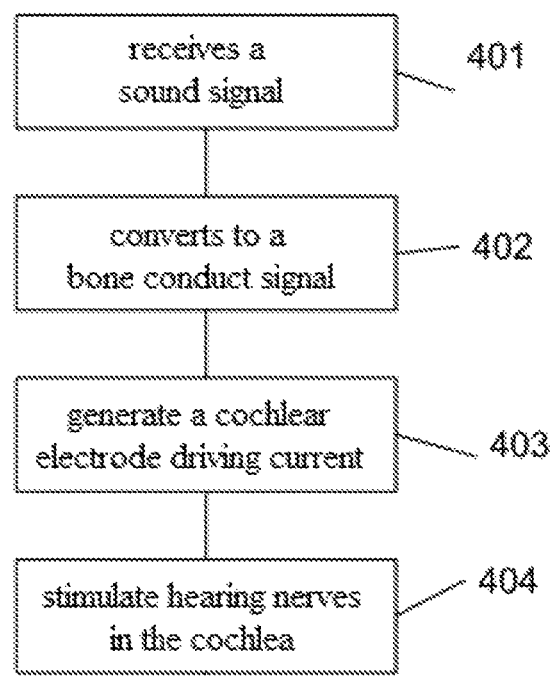
FIG. 5 illustrates a flow chart of an embodiment of present invention.

FIG. 5 is an embodiment of one hearing auxiliary processing method according to the present invention. In this embodiment, first of all, a sound signal is received through the bone conduct transceiver (step 401). The received sound signal is treated as a sound raw data, and the bone conduct transceiver converts the sound raw data to a corresponding bone conduct signal (step 402), to facilitate transmission. When the receiver, which installed to an inner ear portion of the person with hearing impairment, receives this bone conduct signal, the receiver will convert the bone conduct signal to a sound restoration signal. Then the driver can generate a corresponding cochlear electrode driving current as a physical signal according to the sound restoration signal (step 403). Then, such a cochlear driving current can serve as a physical signal to stimulate hearing nerves in the cochlea to obtain hearing for the person with hearing impairment (step 404).

Figure 6:
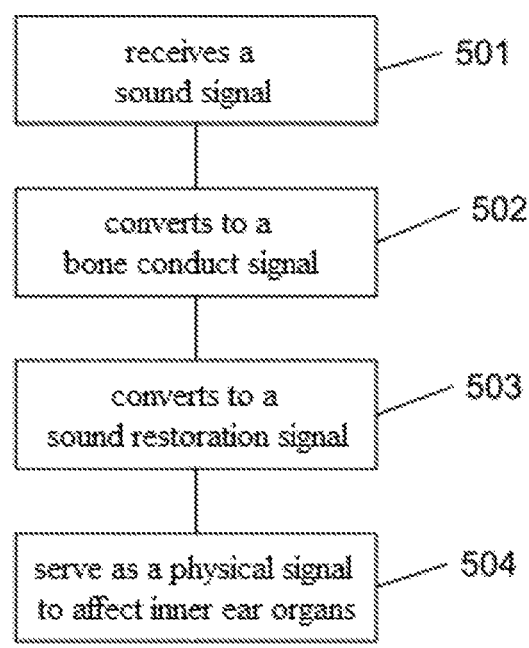
FIG. 6 illustrates a flow chart of another embodiment of present invention.

FIG. 6 is an embodiment of another hearing auxiliary processing method according to the present invention. In this embodiment, at first, a sound signal is received through the bone conduct transceiver as mentioned above (step 501). The received sound signal is taken as a sound raw data, and the bone conduct transceiver converts such a sound raw data to a bone conduct signal correspondingly (step 502), to facilitate transmission. When the receiver installed to an inner ear portion of the person with hearing impairment receives this bone conduct signal, the receiver will convert the bone conduct signal to a sound restoration signal, and then according to the sound restoration signal, through a driver, can generate an amplified corresponding sound wave vibrating signal as a physical signal (step 503). Then, such a sound wave vibrating signal can serve as a physical signal to affect inner ear organs and other hearing receivers, to cause the person with hearing impairment to obtain a hearing signal (step 504).

Figure 7:
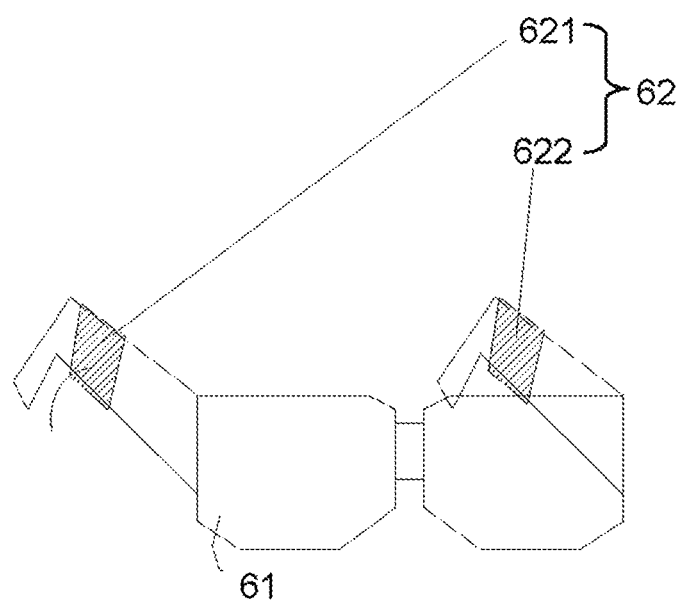
FIG. 7 illustrates a schematic diagram of another embodiment of present invention.

FIG. 7 illustrates that a bone conduct transceiver 61 can be made into a shape of a pair of glasses or disposed the bone conduct transceiving module 62 on a pair of glasses, to allow the person with hearing impairment to wear it in a manner of glasses. The bone conduct transceiving module 62 clings to the skin near the ears. The bone conduct transceiving module 62 triggers the corresponding tiny bone to vibrate, and the bone conduct signal will be transferred to the receiver and the driver placed in the inner ear to produce hearing for the user.

Human can recognize the small differences between the sounds received by different ears, and establish perception for a three-dimensional space. The bone conduct transceiver 62 can have a first transceiving component 621 and a second transceiving component 622. The first transceiving component 621 and the second transceiving component 622 is disposed respectively to two ears of the person with hearing impairment. Moreover, to avoid that the first transceiving component 621 and the second transceiving component 622 interfere with each other in signal transmission, the bone conduct signal from the first transceiving component 621 and the second transceiving component 622 have a transmitting shift that is staggered apart, for example, the signal is transmitted in a manner of time-division multiplexing.

In another practice, the bone conduct transceiver 62 has a first transceiving component 621 and a second transceiving component 622. The first transceiving component 621 and the second transceiving component 622 is respectively disposed correspondingly to two ears of the person with hearing impairment. The first transceiving component 621 and the second transceiving component 622 may employ different signal aspects, to avoid that the first transceiving component 621 and the second transceiving component 622 interfere with each other in signal transmission. For example, the first transceiving component 621 and the second transceiving component 622 use carriers at different frequencies to carry the bone conduct signal, and through the arrangement of different signal aspects, mutual interference between signals is avoided.

Another method that replaces glass wearing is attaching one magnet to a transceiving component (or the first transceiving component 621 and the second transceiving component 622) of the bone conduct transceiver 62 and implanting another magnet below the scalp of the person with hearing impairment through a surgery. The bone conduct transceiver 62 or its transceiving component will be attached to the scalp of the person with hearing impairment through magnetic force.

Bone conduction is a sound conduction manner, that is, sound waves are transferred by converting sounds to mechanical vibration at different frequencies and through a person's skull, bony labyrinth, lymph fluid of coclea, spiral organs, auditory nerves and hearing center. Contrast to generate sound waves through a vibrating diaphragm, bone conduction saves many steps of sound wave transmission and could achieved clear sound restoration in noisy environments. Furthermore, the sound waves may not be affected other people because of diffusion in the air.

A bone conduct technology is divided into a bone conduct speaker technology and a bone conduct microphone technology.

The technique of bone conduct speaker is used for receiving sounds, in other way of speaking this technique is meant for ones to hear. The principle of air conduction speaker is to convert electric signals to sound waves (vibrating signals) and transmit to auditory nerves. On the other hand, the principle of the bone conduct speaker is to directly convert electric signals to sound waves (vibrating signals), and the sound waves are transmit to auditory nerves through bones. In these two methods, the transmitting mediums of the sound waves (vibrating signals) are different.

The technique of bone conduct microphone is used for receiving sounds, in other way of speaking this technique is meant for ones to hear. Air conduction transmitting transfers sound waves to a microphone through air, while bone conduction transmitting transfers sound waves directly through bones.

Specifically, the implementation example can be actually made into an external electronic ear device, used in an artificial ear system. The external electronic ear device includes a housing, an external magnet, a microphone, a processing circuit and a wireless circuit.

The external magnet is installed to a predetermined position at the housing, used to interact with a receiver magnet installed to an inner side of scalp of a user. The housing could be attached to the outer surface of the scalp of the user. The receiver magnet belongs to an implanted artificial ear device. The microphone is installed to a predetermined position of the housing, used to receive an outside sound and generate a corresponding sound signal. The microphone may be various directed or undirected reception devices, and can convert an outside sound to a corresponding sound signal. The microphone may be one or may be a combination of multiple microphones. The processing circuit is installed at the housing and converts the sound signal to a bone conduct signal. The processing signal may include a microcontroller, or an Application Specific Integrated Circuit (ASIC). The processing signal may be totally or partly hardware circuit logic to match corresponding software logic. The bone conduct signal is transferred to the implanted artificial ear device, and the implanted artificial ear device converts an electrode driving signal to multiple electrode currents, that is, more than one electrode current. Through the corresponding multiple electrodes, multiple electrical stimulations are produced at a cochlear nerve conduction part, to cause the user to produce a hearing corresponding to the outside sound.

In practice, the housing has a shell shape, and the shell shape can be tailor-made for a the user according to the attaching position of the head and the color and shape of the housing could be substantially similar to those of the head attaching position, so that the shell shape is not easy to perceive.

In addition, wigs may also be attached to the housing, so that the shell shape of the housing is not easy to perceive.

The present invention is described as above with the foregoing preferred embodiments, but the embodiments are not intended to limit the present invention. Any person skilled in the art can make some variations and modifications without departing from the spirit and scope of the present invention. Therefore, the patent protection scope of the present invention should be subject to that defined by the claims appended to the specification.

What is claimed is:

1. A hearing auxiliary device for helping a person with hearing impairment to obtain hearing information, comprising:
    a bone conduct transceiver, converting a sound raw data to a bone conduct signal;
    a receiver, configured to be installed to an inner ear portion of the person with hearing impairment for receiving the bone conduct signal through bone conduction, and converting the bone conduct signal to a sound restoration signal; and
    a driver, sending out a physical signal according to the sound restoration signal in order to let the person with hearing impairment to obtain a hearing signal, wherein the bone conduct transceiver has a first transceiving component and a second transceiving component, the first transceiving component and the second transceiving component respectively corresponding to two ears of the person with hearing impairment, and the first transceiving component and the second transceiving component use carriers at different frequencies to carry the bone conduct signal, to avoid the first transceiving component and the second transceiving component interfering with each other during signal transmission.

2. The hearing auxiliary device according to claim 1, wherein the receiver is configured to be installed to a through hole on the eardrum of the person with hearing impairment.

3. The hearing auxiliary device according to claim 1, wherein the driver is configured to be installed to a cochlea of the person with hearing impairment.

4. The hearing auxiliary device according to claim 1, wherein the bone conduct signal is a signal undergoing compression and error-correcting code.

5. The hearing auxiliary device according to claim 1, wherein the bone conduct transceiver further comprises a parameter adjuster, and via the parameter adjuster, an optimization processing can be made for cranial electrical characteristics of the person with hearing impairment.

6. The hearing auxiliary device according to claim 1, wherein the bone conduct transceiver further comprises a parameter adjuster, which sends a testing signal to the receiver, then the bone conduct transceiver receives a testing result from the receiver, and adjusts the bone conduct signal accordingly.

7. The hearing auxiliary device according to claim 1, wherein the bone conduct transceiver is installed to a pair of glasses, to allow the person with hearing impairment to wear it in a manner of glasses.

8. The hearing auxiliary device according to claim 1, wherein the bone conduct transceiver is configured to be attached to scalp of the person with hearing impairment via magnetic force.

9. A hearing auxiliary processing method for helping a person with hearing impairment to obtain hearing information, comprising:
    converting a sound raw data to a bone conduct signal via a bone conduct transceiver;

receiving the bone conduct signal through a receiver installed to an inner ear portion of the person with hearing impairment through bone conduction, and converting the bone conduct signal to a sound restoration signal; and according to the sound restoration signal, the driver sending out a physical signal in order to let the person with hearing impairment to obtain a hearing signal, wherein the bone conduct transceiver has a first transceiving component and a second transceiving component, the first transceiving component and the second transceiving component respectively corresponding to two ears of the person with hearing impairment, and the first transceiving component and the second transceiving component use carriers at different frequencies to carry the bone conduct signal, to avoid the first transceiving component and the second transceiving component interfering with each other during signal transmission.

10. The hearing auxiliary processing method according to claim 9, wherein the receiver is installed to a through hole on the eardrum of the person with hearing impairment.

11. The hearing auxiliary processing method according to claim 9, wherein the driver is installed to a cochlea of the person with hearing impairment.

12. The hearing auxiliary processing method according to claim 9, further comprising performing compression and error-correcting code on the bone conduct signal.

13. The hearing auxiliary processing method according to claim 9, further comprising optimizing procession for cranial electrical characteristics of the person with hearing impairment, for adjusting corresponding parameters.

14. The hearing auxiliary processing method according to claim 9, further comprising sending a testing signal to the receiver, receiving a testing result from the receiver, and adjusting the bone conduct signal according to the testing result.

15. The hearing auxiliary processing method according to claim 9, wherein the bone conduct transceiver is installed to a pair of glasses, to allow the person with hearing impairment to wear it in a manner of glasses.

16. The hearing auxiliary processing method according to claim 9, wherein the bone conduct transceiver is attached to scalp of the person with hearing impairment via magnetic force.

* * * * *